(12) United States Patent
Wixey et al.

(10) Patent No.: US 7,478,635 B2
(45) Date of Patent: Jan. 20, 2009

(54) BREATHING ASSISTANCE APPARATUS

(75) Inventors: David Fraser Wixey, Auckland (NZ); Ian Douglas Makinson, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 421 days.

(21) Appl. No.: 10/534,561

(22) PCT Filed: Oct. 29, 2003

(86) PCT No.: PCT/NZ03/00243

§ 371 (c)(1), (2), (4) Date: Sep. 22, 2005

(87) PCT Pub. No.: WO2004/043528

PCT Pub. Date: May 27, 2004

(65) Prior Publication Data
US 2006/0130836 A1 Jun. 22, 2006

(30) Foreign Application Priority Data
Nov. 12, 2002 (NZ) .................................... 522577
Sep. 26, 2003 (NZ) .................................... 528536

(51) Int. Cl.
*A61M 11/00* (2006.01)
(52) U.S. Cl. .................. 128/203.17; 128/204.23
(58) Field of Classification Search ........ 128/204.22, 128/203.12, 203.16, 203.17, 204.23, 204.14
See application file for complete search history.

(56) References Cited

U.S. PATENT DOCUMENTS

| 5,558,084 | A | * | 9/1996 | Daniell et al. ........... 128/203.17 |
| 6,050,260 | A | | 4/2000 | Daniell et al. |
| 2002/0077856 | A1 | | 6/2002 | Pawlikowski et al. |

FOREIGN PATENT DOCUMENTS

| DE | 19630466 | 2/1998 |
| JP | 9276408 | 10/1997 |
| WO | WO 01/10489 | 2/2001 |
| WO | WO 02/49259 | 6/2002 |

* cited by examiner

*Primary Examiner*—Steven O Douglas
(74) *Attorney, Agent, or Firm*—Trexler, Bushnell, Giangiotgi, Blackstone & Marr, Ltd.

(57) ABSTRACT

The present invention may include an integral, separable or separate humidifier (100) which may be selectively configured to an inoperative or operative state. The switch over is dependent on the user or the seller having access to an actuation tool to activate the humidifier. The Continuous Positive Airway Pressure (CPAP) device is initially available for use as a standalone CPAP (100). The heater plate being isolated by a covering shroud (102), the shroud (102) also forms a connection port for the CPAP blower outlet (104). The heated humidification hardware being disabled by the absence of the activation tool. Upgrade to a CPAP device including heated humidification is completed by the installation of the actuation tool. Removal of the heater plate isolating shroud and/or installing the actuation tool enables the software controlled heated humidification hardware for heated humidifier operation. Other upgrades to functionality are also disclosed.

17 Claims, 3 Drawing Sheets

BREATHING ASSISTANCE APPARATUS

FIELD OF INVENTION

The present invention relates to humidification particularly though not solely to humidifying gases to a user requiring Continuous Positive Airway Pressure (CPAP).

SUMMARY OF THE PRIOR ART

It is known in the art to provide CPAP treatment in conjunction with humidity, see for example U.S. Pat. No. 6,050,260. The humidification is usually provided either by:
1. An integrated CPAP blower and humidifier as described in U.S. Pat. No. 6,050,260, whereby there is no separation of the CPAP and heated humidifier except for the humidification chamber for filling and cleaning.
2. A standalone CPAP device connected by a flexible airway tube to a standalone heated humidifier, the equipment generally mounted on a tray for stability.
3. A CPAP device that can standalone but can also be attached to a modular heated humidifier. No flexible airway tube nor mounting tray is required.

It would be desirable to provide a CPAP device which could be easily upgraded to provide humidification.

SUMMARY OF THE INVENTION

It is an object of the present invention to provide a breathing assistance apparatus which goes someway to achieving the abovementioned desiderata, overcoming the abovementioned disadvantages or at least provides the public with a useful choice.

Accordingly in a first aspect the invention consists in a breathing assistance apparatus comprising:
a gas delivery device adapted to provide gas at a substantially positive mean pressure;
a humidifier adapted to humidify said gas and;
wherein said apparatus is configurable to at least two configurations, a first configuration with a predetermined functionality inoperable with said gas delivery device operable and a second configuration with said predetermined functionality and said device operable.

In a second aspect the invention consists in a breathing assistance apparatus comprising:
means for providing gas at a substantially positive mean pressure;
means for humidifying said gas; and
means for providing at least two configurations, a first configuration with a predetermined functionality inoperable and a second configuration with said predetermined functionality.

In a third aspect the invention consists in a method of delivering respiratory gases to a patient comprising the steps of:
providing gas at a substantially positive mean pressure;
humidifying said gas; and
providing at least two configurations, a first configuration with a predetermined functionality inoperable and a second configuration with said predetermined functionality.

Wherein said predetermined functionality is active humidification and said second configuration occurs by the engagement of a predetermined mechanical key with said apparatus.

Wherein said predetermined functionality is active humidification and said second configuration occurs by the engagement of a predetermined mechanical key with said apparatus said second configuration occurs by the engagement of a predetermined magnetic key with said apparatus.

Wherein said predetermined functionality is active humidification and said second configuration occurs by the engagement of a predetermined mechanical key with said apparatus said second configuration occurs by the entry of a predetermined code into a keypad.

Wherein said predetermined functionality is active humidification and said second configuration occurs by the engagement of a predetermined mechanical key with said apparatus a portion of said apparatus may be separated corresponding to said first configuration, whereby the integration of said portion corresponds to said second configuration.

Wherein said predetermined functionality is active humidification and said second configuration occurs by the engagement of a predetermined mechanical key with said apparatus said second configuration occurs by introducing a software or hardware dongle.

Wherein said apparatus further comprises a conduit between the device and the patient and said predetermined functionality is active humidification and heater within or incorporated with said conduit.

Wherein said predetermined functionality relates to heating said gas and said second configuration relates to energising said heater to heat said conduit and/or said gas directly.

Wherein said predetermined functionality relates to storage or display of data relating to the use of said apparatus and said second configuration relates to energising a display to indicate said use.

Wherein said predetermined functionality relates to the pressure level, delivered to the patient and said second configuration relates to providing either a continuous or stepwise correction in sound pressure level.

In a fourth aspect the invention consists in a apparatus for delivering gas to a patient comprising a gas delivery device configured to provide gas at a predetermined pressure level,
a heater,
a chamber having an inlet and an outlet,
said inlet configured to receive gas from said device,
including a body of water whereby said body of water being heated by said heater providing vapour within said chamber thereby humidifying gases passing from said inlet to said outlet,
a controller or processor configured to energise said heater according to at least a user selectable level,
a cover configured to prevent user selection of said heating level and providing an outlet directly from said device,
wherein when said chamber is installed in proximity to said heater said apparatus delivers humidified gas to a patient at a predetermined pressure level,
and when said chamber is removed and said cover is installed said apparatus delivers unhumidified gas to a patient at a predetermined pressure level.

Wherein said cover may be removed using a mechanical key to disengage it with said apparatus.

Wherein said apparatus further comprises a control input configured to provide user selection to said controller.

Wherein said input may be locked to prevent user input and unlocked by engaging a mechanical key with said input.

In a fifth aspect the invention consists in a apparatus for delivering gas to a patient comprising a gas delivery device configured to provide gas at a predetermined pressure level,
a heater,
a chamber having an inlet and an outlet,
said inlet configured to receive gas from said device, including a body of water whereby said body of water being heated by said heater providing vapour within said chamber thereby humidifying gases passing from said inlet to said outlet, a controller or processor configured to energise said heater according to at least a user selectable level.

a user input configured to selectively enable or disable said heater and/or other functionality associated with said apparatus.

Wherein said apparatus further comprises a display adapted to indicate the current level of functionality enabled.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION

A typical integrated CPAP humidifier is described in U.S. Pat. No. 6,050,260. The contents of which are incorporated herein by reference.

The present invention may include an integral, separable or separate humidifier which may be selectively configured to an inoperative or operative state. The switch over is dependent on the user or the seller having access to an actuation tool (described later) to activate the humidifier.

Figure 1:
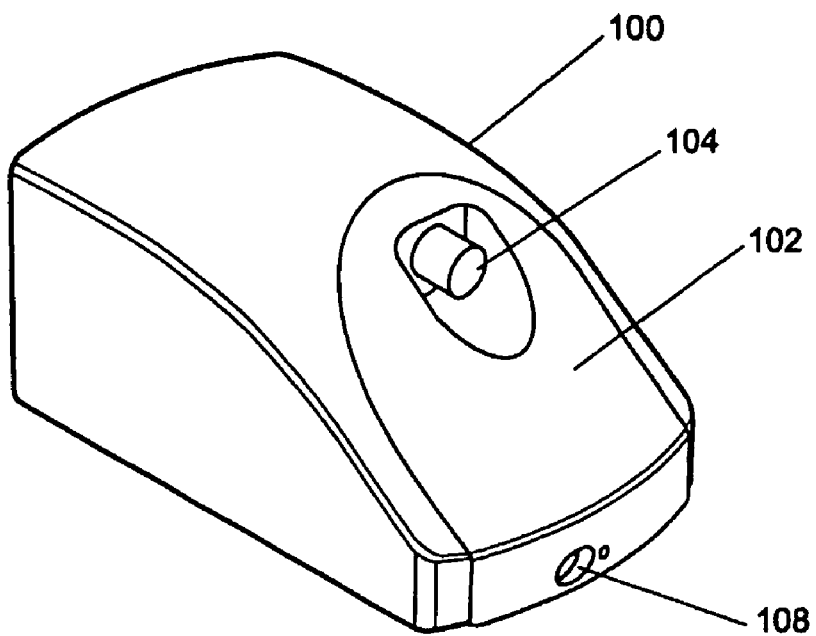
FIG. 1 is a perspective view of the CPAP only configuration.

Referring to FIG. 1 a CPAP device 100 is initially available for use as a standalone CPAP. In this configuration, the heater plate 106 is isolated by a covering shroud 102. The shroud 102 also forms a connection port 104 for the CPAP blower outlet. The heated humidification hardware is disabled by the absence of the activation tool.

Upgrade to a CPAP device that includes heated humidification is completed by the installation of the actuation tool. Removal of the heater plate isolating shroud 102 shown in FIG. 3, and/or installing the actuation tool enables the software controlled heated humidification hardware for heated humidifier operation.

Examples of the various forms of actuation tool could include:

1. Software Key via Serial Data Port

The CPAP device could be connected via RS232 serial connection to a computer or directly via TCP/IP or telephone line to the Internet to receive either additional software or coded actuation data.

2. Mechanical Key

Figure 2A:
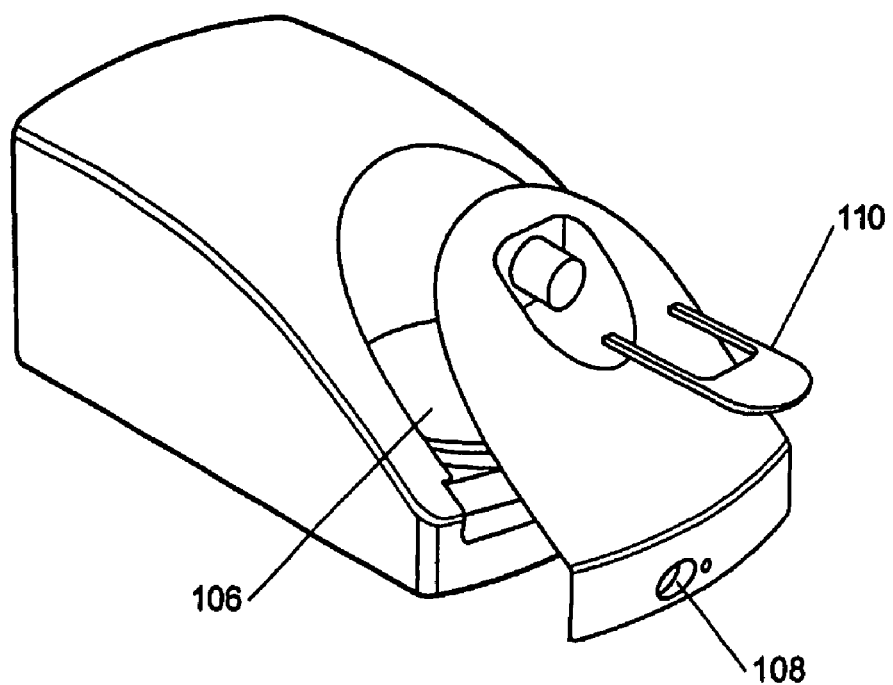
FIG. 2A is a blown out view of the CPAP only configuration.
Figure 2B:
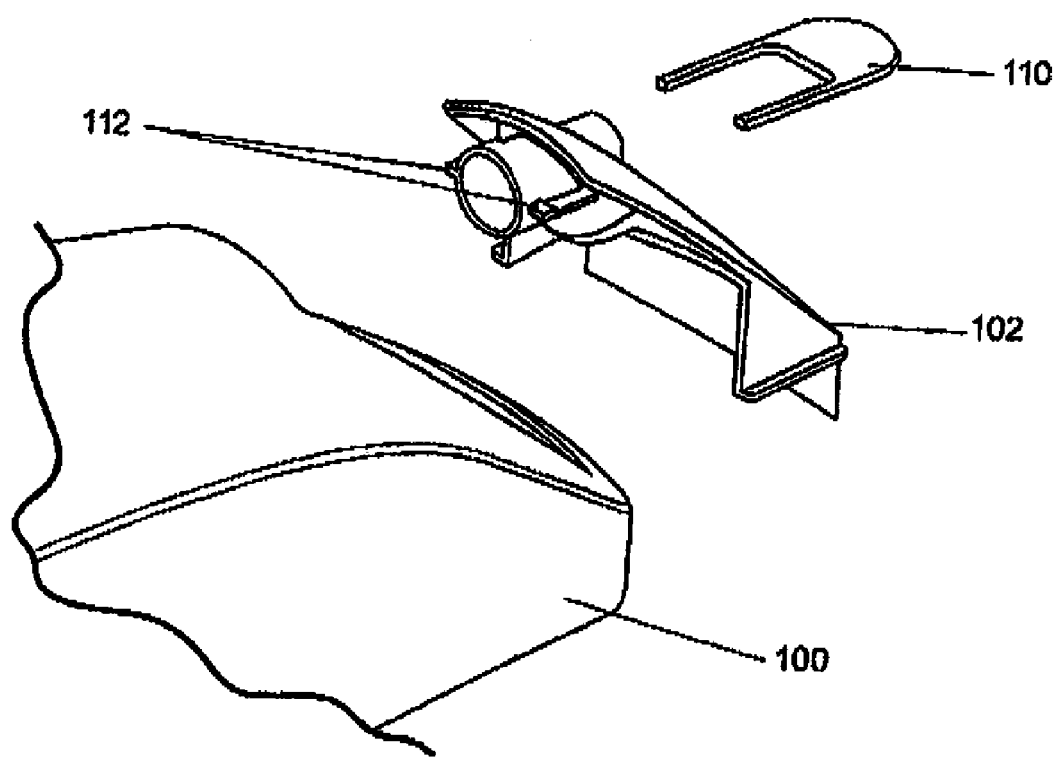
FIG. 2B is a reverse angle of FIG. 2A.

The heater plate vestibule is covered by a shroud 102. A mechanical key (110, FIG. 2A) is used to remove the shroud 102. The heater plate control knob 108 is locked off by the shroud 102 as shown in FIG. 2A. The upgrade kit may include a knob to turn the heater plate 106 on. In one embodiment shown in FIGS. 2A & 2B engaging the key 110 pushes two snap fit flanges 112, allowing the shroud 102 to be removed.

3. Magnetic Key

Also includes a shroud 102 as in FIG. 2 but in addition there is a key which has magnets in a predetermined pattern. This key is slid into a cavity in the case. Inside the case there are Hall effect sensors that defect the pattern of magnets. If the key is detected, the heater plate is activated.

4. Code Number Verification

Also includes a shroud 102 as in FIG. 2 but in addition there is a code number that is entered into the device. The dealer phones a freephone number with the serial number of the CPAP device and pays for the upgrade. The freephone service then gives the dealer a code number that is specific to the serial number of the CPAP device. This code number is then entered into a keypad (not shown) to activate the humidifier.

The freephone service could also be an Internet based service.

Another alternative is that the upgrade kit includes a card with a number hidden inside the packaging. This number then gives the freephone service evidence that the dealer has paid for the kit, and the financial transaction then doesn't have to be conducted on the phone. Similarly to prevent fraud the numbers could be stored such that if a number is used twice an alarm is raised.

5. Dongle

A plug in pack containing an electronic circuit designed to respond in a predetermined way to interrogation by the CPAP device. The plug in pack could plug into a dedicated socket in the device or into the existing serial port. Similarly a smart card of known type could be interfaced with the CPAP device to activate the humidifier.

Additionally, the dongle may contain some of the electronic circuit needed to operate the heater plate. Again a shroud 102 as seen in FIGS. 1 and 2 would be required.

6. Removable Heater Plate

The CPAP device is supplied with a plastic cradle where the heater plate currently is. The plastic cradle has all of the mounting and springing arrangement that the current heater plate has. the cradle also has an electrical connector and clips. A second part consisting of the pressed metal heater plate top surface with the element, thermistor and thermal cutout bonded to it is then supplied in the upgrade kit. The dealer can then remove the shroud and plug the heater plate into the cradle. The plastic cradle means that the fixings and spring mechanism can be preassembled inside the unit so that the heater plate can be installed without tools and without the need to disassemble the unit.

It will be appreciated that while in the preferred embodiment the unhumidified CPAP configuration utilises a shroud 102 over the heater plate, this is not required. The heater plate 106, could be rendered in inoperable/operable by any of the methods described, but with the water chamber 200 in place in both configuration.

7. Cold Passover

Figure 3:
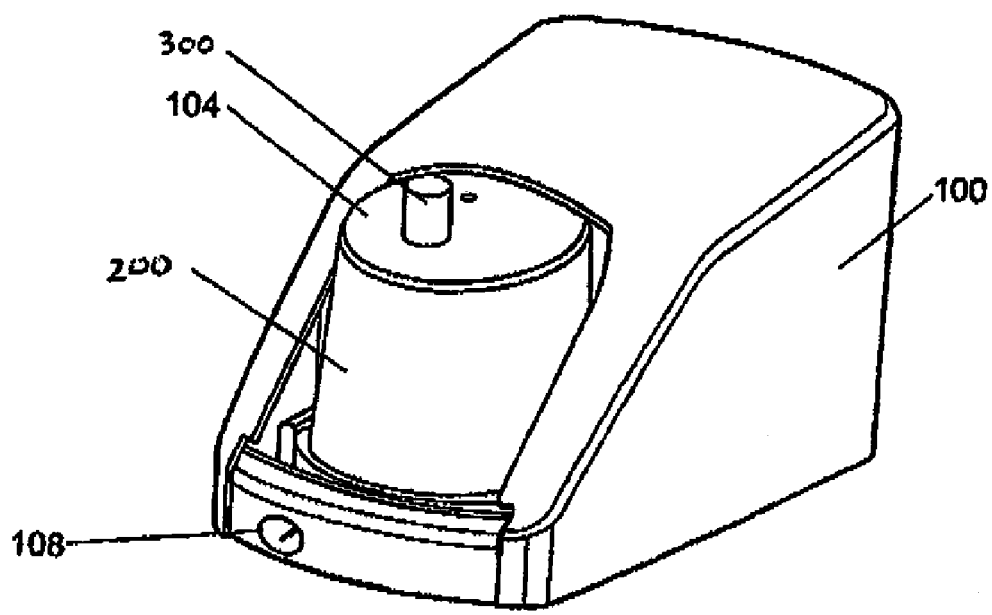
FIG. 3 is a perspective view of the humidified CPAP configuration.
Figure 4:
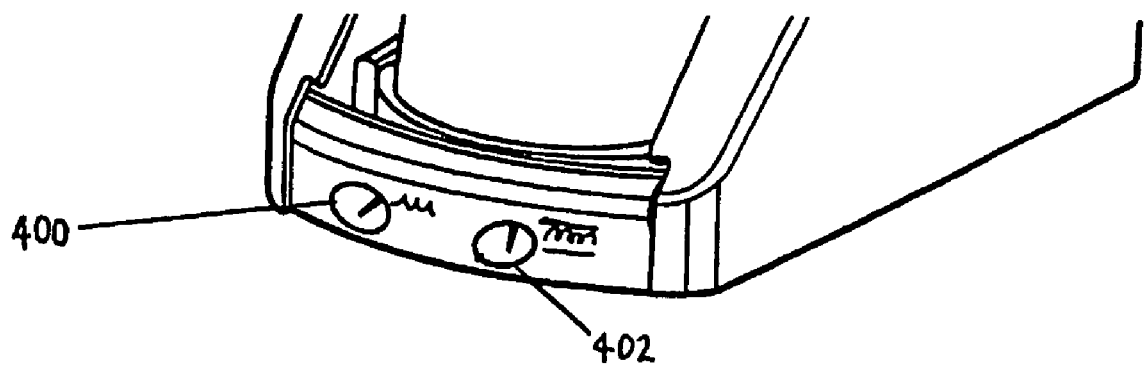
FIG. 4 is a front view showing another example control panel.

Whereas the system in FIG. 3 includes at least the water chamber this could operate in both humidified and non humidified modes. For example the heater plate need not be initially supplied. The heater plate may be supplied but not activated.

Figure 5:
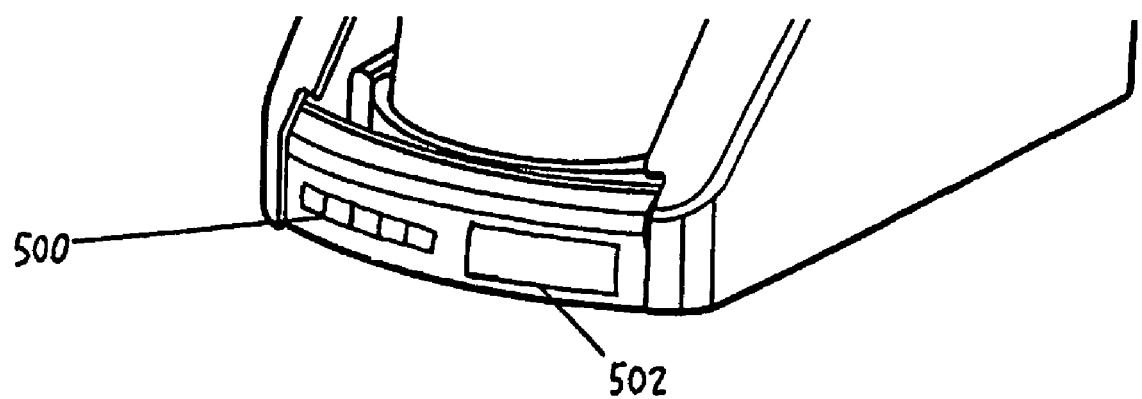
FIG. 5 is a front view showing an alternative control panel.

Activating the heater plate could occur for example:
1. Heater plate control is by a rotary potentiometer 108, 400. This can be incapacitated by a lock to physically prevent the potentiometer from turning. Upgrade to active humidification requires a second key to remove the potentiometer lock and activate the heater.
2. Heater control is by a setting in a menu accessed by buttons. Upgrade to active humidification requires a PIN number to activate the heater plate. Referring to FIG. 5 the key pad 500 is shown.

8. Heated Tube

The system could include a heated tube to deliver the gas to avoid condensation. Again this might be incapacitated initially.

Activating the heated tube control could occur by example:
1. Heater tube control by a rotary potentiometer 402, which is locked to physically prevent the potentiometer from turning. Upgrade requires a third key to remove the heated tube potentiometer lock and activate the heated tube.
2. Heated tube control by a setting in a menu accessed by buttons. Upgrade requires a PIN number to activate the heated tube.

Example upgrade kits could be:

Cold passover kit: Contains a chamber, key #1 to remove cover.

Heated humidification kit: Contains chamber, key #1 to remove cover and key #2 to remove the potentiometer lock OR a PIN number to activate the heater.

Heated tube kit: Contains chamber, key #1 to remove cover, key #2 to remove the potentiometer lock OR a PIN number to activate the heater. Key #3 to remove the heated tube potentiometer lock OR a second PIN number.

9. Other Functionality Upgrade

The electronic or mechanical key could also be used to upgrade other functionality. For example the applicant has identified it might be desirable to store and/or display data in relation to patient compliance, or use of the treatment.

Referring to FIG. 5 we see a screen 502 for display of such compliance data. Depending on the key used example levels of functionality are given below:

Option 1: Machine displays no information.
Option 2: Machine displays machine run time only.
Option 3: Machine displays summary data on the display. For example, average hours complied per night used.
Option 4: Full compliance data download. All the day to data stored in the machine can be downloaded to a PC for analysis. Summary data would also be displayed.

It would be possible to activate any of these options by entering a suitable PIN number, or any other method, previously described or not.

This method could also apply to upgrading any function of the machine for example different levels of delivered pressure for inhalation versus exhalation and automatically calibrating the pressure level depending on symptoms exhibited by the patient.

The invention claimed is:

1. An integrated breathing assistance apparatus for use as part of a system for providing respiratory gases to a user, comprising:
    a gases delivery device adapted to provide respiratory gases at a substantially positive mean pressure through an outlet,
    a heater plate, adapted to receive a water chamber and heat the contents of said chamber in use, said gases delivery device and said heater plate rigidly connected together,
    a controller adapted to energise said integrated breathing assistance apparatus to at least two configurations, a first configuration where said gases delivery device is operable to provide respiratory gases at a substantially positive mean pressure through said outlet and said heater plate is non-operable, and a second configuration where said gases delivery device is operable to provide respiratory gases at a substantially positive mean pressure through said outlet, and said heater plate is also operable,
    said controller configuring said apparatus into said second configuration when an activation tool is engaged with the apparatus,
    said controller configuring said apparatus to said first configuration when said activation tool is absent.

2. An apparatus as claimed in claim 1 wherein said apparatus includes said activation tool and said apparatus further includes a communication port,
    said activation tool being a software key, in use a user communicating said software key to said controller via said communication port so that said controller configures said apparatus into said second configuration.

3. An apparatus as claimed in claim 1 wherein said apparatus further includes a shroud, said shroud adapted to cover said heater plate and lock to said apparatus, a user unlocking said shroud using a mechanical key and removing said shroud from said apparatus when a user wishes to use said apparatus in said second configuration.

4. An apparatus as claimed in claim 3 wherein said apparatus inches hall affect sensors in communication with said controller, and said activation tool is a magnetic key having magnets arranged in a predetermined pattern, said hall effect sensors arranged so as to detect said magnets when said key is engaged with said apparatus, in use a user engaging said activation tool with said apparatus so that said controller configures said apparatus into said second configuration.

5. An apparatus as claimed in claim 3 wherein said apparatus includes a communication port, and said activation tool is a dongle containing an electronic circuit, said electronic circuit and said controller mutually adapted to communicate with one another when said dongle is engaged with said apparatus via said communication port, said electronic circuit providing a predetermined response to interrogation by said controller, in use a user engaging said dongle with said communication port so that said controller configures said apparatus into said second configuration upon receipt of said predetermined response.

6. An apparatus as claimed in claim 3 wherein said heater plate is repeatedly removable and replaceable from said apparatus, said heater plate being adapted to integrate with said apparatus once said shroud is removed, integration of said removable heater plate with said apparatus enabling said controller so that said controller configures said apparatus into said second configuration.

7. An apparatus as claimed in claim 3 wherein said apparatus includes a user-operable key pad in communication with said controller, said activation tool being a PIN, said controller configuring said apparatus into said second configuration when a use enters a PIN via said key pad.

8. An apparatus as claimed in any one of claims 3 to 7 wherein said apparatus is adapted to connect to a conduit, said conduit providing said gases to a user, said conduit having a conduit heater,
   said conduit heater being inoperable in said first and second configurations,
   said apparatus being configurable to a third configuration wherein said gases delivery device is operable and said heater plate is operable and said conduit heater is operable,
   said controller configuring said apparatus to said third configuration when one of said activation tool and a second activation tool is engaged with the apparatus.

9. An apparatus as claimed in claim 8 wherein said apparatus further includes a user-operable key pad in communication with said controller, said second activation tool being a conduit heater PIN, said controller configuring said apparatus into said third configuration when a user enters said conduit heater PIN via said key pad.

10. An integrated breathing assistance apparatus for use as part of a system for providing respiratory gases to a user, comprising:
    a gases delivery device for providing gases at a predetermined pressure level,
    a heater plate adapted to receive a water chamber and heat the contents of said chamber in use, said gases delivery device and said heater plate rigidly connected together,
    a controller configured to energise said heater according to at least a user selectable level,
    a removable cover configured to prevent user selection of said user selectable level and provide an outlet from said gas delivery device, wherein
    when said cover is installed, said apparatus is adapted to deliver un-humidified gases via said outlet at a predetermined pressure level, and
    when said cover is removed and at least a humidification chamber containing water is installed in proximity to said heater, said chamber having a chamber inlet and a chamber outlet, said chamber inlet being configured to receive gases from said gas delivery device, said apparatus is adapted to deliver humidified gases via the chamber outlet.

11. An apparatus as claimed in claim 10 wherein said cover is adapted to lock to said apparatus, a user unlocking the cover using a mechanical key to remove the cover from said apparatus.

12. An apparatus as claimed in claim 11 further comprising a control input configured to provide user selection of said user selectable level to said controller.

13. An apparatus as claimed in claim 12 wherein said control input may be locked to prevent user selection of said user selectable level and unlocked to allow user selection of said user selectable level, said control input being unlocked by engaging a control input mechanical key with said apparatus.

14. An apparatus as claimed in claim 10 wherein said heater plate is repeatedly removable and replaceable from said apparatus, said heater plate being adapted to integrate with said apparatus once said cover is removed.

15. An apparatus as claimed in any one of claims 10 to 14 wherein the chamber outlet is adapted to be connected to a conduit, the conduit providing said gases to a user, the conduit having a conduit heater for heating the gases in the conduit,
    the controller being configured to energise said conduit heater according to at least a user selectable conduit heating level,
    the apparatus having a conduit heater control input configured to provide user selection of said conduit heating level.

16. An apparatus as claimed in claim 15 wherein said conduit heater control input may be locked to prevent user selection of said conduit heating level and unlocked to allow user selection of said conduit heating level, said conduit heater control input being unlocked by engaging a conduit heater control input mechanical key with said apparatus.

17. A method of controlling an apparatus for delivering respiratory gases to a patient comprising the steps of:
    energising a gases delivery device to provide gases at a positive mean pressure;
    configuring the apparatus to energise a humidifier based on the presence of an activation tool, said humidifier being adapted to or adaptable to humidify said gases to a humidification level,
    providing the respiratory gases un-humidified at a positive mean pressure with the absence of the activation tool, and
    providing the respiratory gases at a positive mean pressure humidified to the humidification level with the engagement of the activation tool with the apparatus.

* * * * *